(12) United States Patent
Gildenblat et al.

(10) Patent No.: US 11,756,677 B2
(45) Date of Patent: Sep. 12, 2023

(54) SYSTEM AND METHOD FOR INTERACTIVELY AND ITERATIVELY DEVELOPING ALGORITHMS FOR DETECTION OF BIOLOGICAL STRUCTURES IN BIOLOGICAL SAMPLES

(71) Applicant: DeePathology Ltd., Ra'anana (IL)

(72) Inventors: Jacob Gildenblat, Holon (IL); Nizan Sagiv, Ga'ash (IL); Chen Sagiv, Ga'ash (IL); Ido Ben Shaul, Ramat HaSharon (IL)

(73) Assignee: DEEPATHOLOGY LTD., Ra'anana (IL)

( * ) Notice: Subject to any disclaimer, the term of this patent is extended or adjusted under 35 U.S.C. 154(b) by 0 days.

(21) Appl. No.: 17/874,948

(22) Filed: Jul. 27, 2022

(65) Prior Publication Data

US 2022/0366710 A1  Nov. 17, 2022

Related U.S. Application Data

(63) Continuation of application No. 17/792,897, filed as application No. PCT/IL2021/050052 on Jan. 17, 2021, now abandoned.

(51) Int. Cl.
*G06K 9/00* (2022.01)
*G16H 30/40* (2018.01)
(Continued)

(52) U.S. Cl.
CPC .......... *G16H 30/40* (2018.01); *G06F 18/217* (2023.01); *G06F 18/2148* (2023.01); *G06F 18/28* (2023.01); *G06F 18/40* (2023.01);

*G06N 3/04* (2013.01); *G06N 3/08* (2013.01); *G06V 10/44* (2022.01); *G06V 10/764* (2022.01);
(Continued)

(58) Field of Classification Search
None
See application file for complete search history.

(56) References Cited

U.S. PATENT DOCUMENTS 10,719,301 B1 * 7/2020 Dasgupta ............. G06V 10/774
2005/0286772 A1   12/2005 Albertelli
(Continued)

FOREIGN PATENT DOCUMENTS

WO  2019026081 A2  2/2019
WO  2019110583 A1  6/2019

OTHER PUBLICATIONS

Qu et al., Joint segmentation and fine-grained classification of nuclei in histopathology images, ISBI 2019 (Year: 2019).*
(Continued)

*Primary Examiner* — Soo Jin Park
(74) *Attorney, Agent, or Firm* — The Roy Gross Law Firm, LLC; Roy Gross

(57) ABSTRACT

A method for categorizing biological structure of interest (BSOI) in digitized images of biological tissues comprises a stage of identifying BSOIs in digitized images and further comprises presenting an image from the plurality of images that comprises at least one BSOI with high level of entropy to a user, receiving from the user input indicative of a category to be associated with the BSOI that had the high level of entropy and updating the cell categories classifier according to the category of the BSOI provided by the user.

7 Claims, 11 Drawing Sheets

(51) Int. Cl.

| | | |
|---|---|---|
| *G06N 3/08* | (2023.01) | |
| *G06N 3/04* | (2023.01) | |
| *G16H 50/20* | (2018.01) | |
| *G06V 20/69* | (2022.01) | |
| *G06V 10/778* | (2022.01) | |
| *G06V 10/44* | (2022.01) | |
| *G06V 10/764* | (2022.01) | |
| *G06F 18/28* | (2023.01) | |
| *G06F 18/40* | (2023.01) | |
| *G06F 18/21* | (2023.01) | |
| *G06F 18/214* | (2023.01) | |
| *G06V 10/80* | (2022.01) | |
| *G06V 10/82* | (2022.01) | |

(52) U.S. Cl.
CPC ........ *G06V 10/7796* (2022.01); *G06V 10/809* (2022.01); *G06V 10/82* (2022.01); *G06V 20/693* (2022.01); *G06V 20/695* (2022.01); *G06V 20/698* (2022.01); *G16H 50/20* (2018.01); *G06V 2201/03* (2022.01)

(56) References Cited

U.S. PATENT DOCUMENTS

| | | |
|---|---|---|
| 2017/0169567 A1 | 6/2017 | Chefd'hotel et al. |
| 2018/0165809 A1 | 6/2018 | Stanitsas et al. |
| 2020/0342597 A1* | 10/2020 | Chukka .................. G06T 7/194 |
| 2021/0073671 A1 | 3/2021 | Puri et al. |

OTHER PUBLICATIONS

Raczkowski et al., "ARA: accurate, reliable and active histopathological image classification framework with Bayesian deep learning", Scientific Reports 2019 (Year: 2019).*

Raczkowski, Lukasz, et al., "ARA: accurate, reliable and active histopathological image classification framework witt Bayesian deep learning", Scientific Reports, 2019, 9.1: 1-12; Retrieved from the Internet :<URL: https://www.nature.com/articles/s41598-019-50587-1 > Oct. 4, 2019.

PCT International Search Report for International Application No. PCT/IL2021/050052, dated Apr. 28, 2021, 3pp.

PCT Written Opinion for International Application No. PCT/IL2021/050052, dated Apr. 28, 2021, 5pp.

Michael Nalisnik et al: "Interactive phenotyping of large-scale histology imaging data with HistomicsML", Scientific Reports, vol. 7, No. 1, Nov. 6, 2017 (Nov. 6, 2017), XP055707138, DOI: 10.1038/s41598-017-15092-3.

Raczkowski, Lukasz et al: "ARA: accurate, reliable and active histopathological image classification framework with Bayesian deep learning", Scientific Reports, vol. 9, No. 1, Oct. 4, 2019 (Oct. 4, 2019), pp. 1-12, XP055842626, ISSN: 2045-2322, DOI: 10.1038/s41598-019-50587-1.

European Search Report for European Patent Application No. 21741205, dated Jun. 12, 2023, 8pp.

* cited by examiner

SYSTEM AND METHOD FOR INTERACTIVELY AND ITERATIVELY DEVELOPING ALGORITHMS FOR DETECTION OF BIOLOGICAL STRUCTURES IN BIOLOGICAL SAMPLES

CROSS REFERENCE TO RELATED APPLICATIONS

This application is a continuation of U.S. patent application Ser. No. 17/792,897, filed Jul. 14, 2022, which is a National Phase of PCT Patent Application No. PCT/IL2021/050052 having International filing date of Jan. 17, 2021, which claims the benefit of priority under 35 U.S.C. § 119(e) of U.S. patent application Ser. No. 16/742,942, filed Jan. 15, 2020. The contents of the above are all incorporated by reference as if fully set forth herein in their entirety.

BACKGROUND OF THE INVENTION

The invention relates to the application of methods of image processing, computer vision, machine learning and deep learning for creating new algorithms for the detection of specific types of biological specimens (e.g. cells) pathologies in Whole Slide Images (WSI) that may be obtained by scanning biopsies with a digital scanner.

In pharma research and medical diagnosis, the detection and quantification of specific types of biological objects such as cells, e.g. lymphocytes, tissues and the like is important. The usual practice is that an expert in the field of research, e.g. a pathologist, views a slide containing digitized image of the scanned specimen under a microscope and roughly estimates the number and density of the cells of interest. The availability of high resolution digital scanners for pathology that produce digitized WSI allows the development of state of the art Computer Vision and Deep Learning methods for cell detection and quantification.

Different applications require the detection of different cells. Each new cell detection algorithm usually requires two major efforts: the first is the annotation of the cells of interest by an expert pathologist, and the second is the development of specific computer vision and deep learning algorithms tailor made for the detection of the specific cells of interest. Both efforts require dedicated expert teams and resources.

The ability to automatically detect certain types of cells in pathology images and to localize them is of significant interest to a wide range of pharma research and clinical practices. Cell detection is a common task that is routinely performed by pathologists, who examine slides under a microscope and provide an estimation of the quantity and density (or other attributes) of the cells based on their empirical assessments. These assessments are generally time consuming and tedious and are prone to fatigue induced errors.

For example, the presence of tumor-infiltrating lymphocytes (TILs), have become a central research topic in oncology and pathology. Immunohistochemical staining (IHC) is a technique that allows to target specific cell types, including lymphocytes, by attaching a colored label to a specific antigen in (subcompartment of) a cell. In this way, immune cells can be distinguished from other type of cells.

Accurate detection and assessment of presence of lymphocytes in cancer could potentially allow for the design of new biomarkers that can help monitor the rapid progression of a tumor. Moreover, automated tools to quantify the immune cells density and their localization in the proximity of tumor cells might help to predict the presence and development of metastases and overall survival of cancer patients. In addition, it allows personalized treatments that can significantly benefit the patients.

Given the very large amount of lymphocytes (≈100,000) in a single cancer tissue specimen, manual assessment at whole-slide image level is a very tedious, time-consuming, and therefore unfeasible task. Moreover, manual assessment suffers from intra- and inter-observer variability. Consequently, a method for automatic detection and quantification of immune cells is of great research and clinical interest.

Moreover, once a cell detection capability is available various quantitative attributes such as cellular morphology, size, shape and texture can be calculated.

The task of cell detection is a very popular topic in digital pathology. Computer-aided methods provide faster image analysis and can significantly improve the objectivity and reproducibility of cell detection. Moreover, the basic science researchers and clinician scientists can be released from boring and repeated routine efforts. Several approaches have been proposed for automatic cell detection on different types of digitized microscopical specimens and for various types of stained specimens. In many cases, detection algorithms are based on morphological operations, region growing, analysis of hand-crafted features and image classifications.

Cell detection and localization constitute several challenges. First, target cells are surrounded by clutters represented by complex histological structures like capillaries, adipocytes, collagen etc. In many cases, the size of the target cell is small, and consequently, it can be difficult to distinguish from the aforementioned clutter. Second, the target cells can appear very sparsely (only in tens), moderately densely (in tens of hundreds) or highly densely (in thousands) in a typical WSI. Additionally, significant variations in the appearance among the targets can also be seen. Moreover, due to the enormous variability (cell types, stains and different microscopes) and data complexity (cell overlapping, inhomogeneous intensities, background clutters and image artifacts), robust and accurate cell detection is usually a difficult problem that requires a dedicated R&D effort of experienced algorithms developers.

Cell detection methods have evolved from employing hand-crafted features to deep learning-based techniques. Traditional computer vision based cell detection systems adopt classical image processing techniques, such as intensity thresholding, feature detection, morphological filtering, region accumulation, and deformable model fitting. Deep neural networks recently have been applied to a variety of computer vision problems, and have achieved better performance on several benchmark vision datasets. The most compelling advantage of deep learning is that it has evolved from fixed feature design strategies towards automated learning of problem-specific features directly from the training data. By providing massive amount of training images and problem-specific labels, users do not have to go into the elaborate procedure for the extraction of features. Instead, a deep neural network (DNN) is subsequently optimized using a mini-batch gradient descent method over the training data, so that the DNN allows autonomic learning of implicit relationships within the data.

In order to develop deep learning neural network-based cell detection algorithms it is required to first annotate thousands of cells within WSI and then develop a specific cell detection deep learning algorithm. Then, there should be a dedicated R&D effort for the development of the neural network for the detection of the specific cells. This is a major effort that is not readily available for every pathology lab.

There is a need to provide pathologists with a tool that may allow them to dynamically create new algorithms for the detection of specific pathologies. It is further needed to provide a tool for rapid annotation of image patches taken from WSI, as well as a visualization tool for the detected cells.

SUMMARY OF THE INVENTION

A method for categorizing biological structure of interest (BSOI) in digitized images of biological tissues is presented, the method according to some embodiments may comprise detecting, by a generic detector, one or more BSOIs in at least one pre-obtained digitized image of biological tissue from a training set images, extracting, image patches that contain, each, a BSOI, annotating the image patches according to the detected BSOIs, generating a BSOI categories classifier, evaluating by a computing system the quality of the BSOI categories, applying the categories classifier to at least some of the digitized images and identifying BSOIs in digitized images using the cell categories classifier and providing for each identified BSOI its center location and its contour, wherein the applying of the categories classifier comprises applying data balancing mechanism that comprises data weighing component.

In some embodiments the weighing mechanism comprises balancing mechanism configured to balance between the level of entropy of the classified BSOI and the level of imbalance of the classified category in the training set of slides.

In some embodiments the stage of identifying BSOIs in digitized images further comprises presenting an image from the plurality of images that comprises at least one BSOI with high level of entropy to a user, receiving from the user input indicative of a category to be associated with the BSOI that had the high level of entropy and updating the cell categories classifier according to the category of the BSOI provided by the user.

In some embodiments each of the plurality of images comprises, at least one BSOI with high level of entropy.

In some embodiments the order of presenting the images which comprise, each, at least one BSOI with high level of entropy, is responsive to the received user input indicative of a category of a BSOI, so that priority of presenting of images which await presenting to the user and comprise BSOI of the category that was indicated by the user, is made higher in response to the user's input.

In some embodiments the weighing mechanism is configured to apply the function Weight=$E*A+B*(N-E)*P_{minority}$ wherein E=Entropy (class proportion), A=Acquisition function as defined in Active Learning, B=parameter, and $P_{minority}$=output of a neural network that detects cell categories that give the probability for the minority category.

A system for categorizing biological structure of interest (BSOI) in digitized images of biological tissues is presented, the system, according to some embodiments, may include a processor, a memory unit, a storage unit, an input unit, an output unit and program code loadable to the processor and adapted to perform, when executed: detecting, by a generic detector, one or more BSOIs in at least one pre-obtained digitized image of biological tissue from a training set images, extracting, image patches that contain, each, a BSOI, annotating the image patches according to the detected BSOIs, generating BSOI categories classifier, evaluating the quality of the BSOI categories, evaluating, by a computing system, the quality of the BSOI categories, applying the categories classifier to at least some of the digitized images and identifying BSOIs in digitized images using the cell categories classifier and providing for each identified BSOI its center location and its contour, wherein the applying of the categories classifier comprises applying data balancing mechanism that comprises data weighing component.

In some embodiments the weighing mechanism may include balancing mechanism configured to balance between the level of entropy of the classified BSOI and the level of imbalance of the classified category in the training set of slides.

A non-transitory storage device according to some embodiments may include a program code stored thereon, which is adapted to perform, when executed, detecting, by a generic detector, one or more pre-obtained BSOIs in at least one digitized image of biological tissue from a training set images, extracting, image patches that contain, each, a BSOI, annotating the image patches according to the detected BSOIs, generating a BSOI categories classifier, evaluating by a computing system the quality of the BSOI categories, applying the categories classifier to at least some of the digitized images and identifying BSOIs in digitized images using the cell categories classifier and providing for each identified BSOI its center location and its contour, wherein the applying of the categories classifier comprises applying data balancing mechanism that comprises data weighing component.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
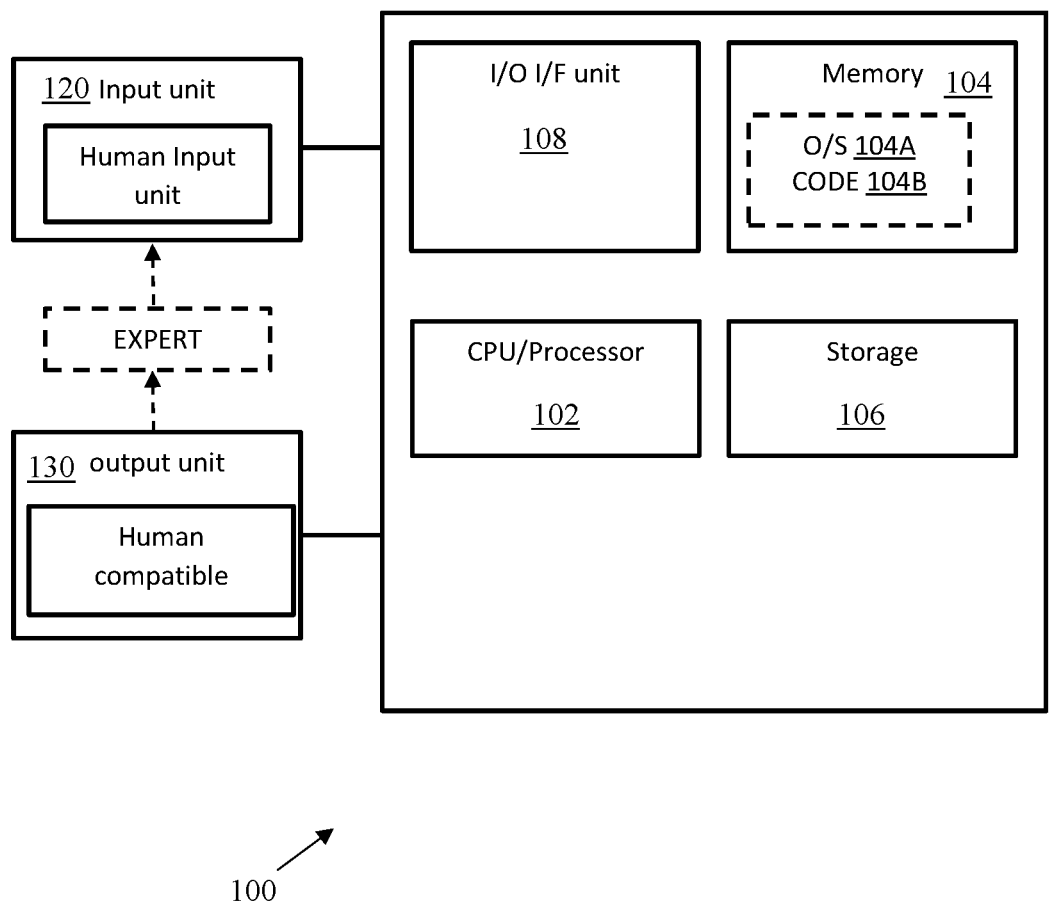
FIG. 1 is a schematic block diagram of a computing system, according to embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

Embodiments of the invention may use a computer, computing platform and the like for carrying out methods and processes described below. Reference is made to FIG. 1, which is a schematic block diagram of computing system 100, according to embodiments of the invention. Computing system 100 may comprise processor 102, memory unit 104, storage device 106 and input/output (I/O) interface (UF) unit 108. Computing system 100 may further comprise input unit 120 and output unit 130.

Processor 102 may be, for example, a central processing unit processor (CPU), a chip or any suitable computing or computational device. Processor 102 (or one or more processors, possibly across multiple units or devices) may be configured to carry out methods described herein, and/or to execute or act as the various modules, units, etc. More than one computing system 100 may be included in, and one or more computing systems 100 may act as the components of a system according to embodiments of the invention.

Memory unit 104 may be or may include, for example, a Random-Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short-term memory unit, a long-term memory unit, or other suitable memory units or storage units. Memory 4 may be or may include a plurality of possibly different memory units. Memory unit 4 may be a computer or processor non-transitory readable medium, or a computer non-transitory storage medium, e.g., a RAM.

Storage unit 106 may be or may include, for example, a flash memory as known in the art, a memory that is internal to, or embedded in, a micro controller or chip as known in the art, a hard disk drive, a CD-Recordable (CD-R) drive, a Blu-ray disk (BD), a universal serial bus (USB) storage device or other suitable removable and/or fixed storage unit. Content may be stored in storage unit 106 and may be loaded from storage unit 106 into memory unit 104 where it may be processed by processor 102. In some embodiments, some of the components shown in FIG. 1 may be omitted. For example, memory unit 104 may be a non-volatile memory having the storage capacity of storage unit 106. Accordingly, although shown as a separate component, storage unit 106 may be embedded or included in memory unit 104.

Computing system 100 may further comprise I/O interface (I/F) unit 108, which is configured to enable communication and connectivity of input unit 120 and output unit 130 to computing system 100. Processor 102, memory unit 104, storage unit 106 and I/O interface unit 108 may be in operational connection with each other.

Input unit 120 may be or may include any suitable input devices, components or systems, e.g., a detachable keyboard or keypad, a mouse, a touch screen, a microphone and the like. Output unit 130 may include one or more (possibly detachable) displays or monitors, speakers and/or any other suitable output devices. Any applicable input/output (I/O) devices may be connected to computing device 1 as shown by blocks 120 and 130. For example, a wired or wireless network interface card (NIC), a universal serial bus (USB) device or external hard drive may be included in input devices 7 and/or output devices 8. It will be recognized that any suitable number of input devices 7 and output device 8 may be operatively connected to computing system 100 as shown by blocks 120 and 130.

Computing system may comprise operating system 104A that may be stored or loaded into memory unit 104. Operating system 104A may be or may include any code segment (e.g., one similar to executable code 104B described herein) designed and/or configured to perform tasks involving coordination, scheduling, arbitration, supervising, controlling or otherwise managing operation of computing system 100, for example, scheduling execution of software programs or tasks or enabling software programs or other modules or units to communicate. Operating system 104A may be a commercial operating system. It will be noted that an operating system 104A may be an optional component, e.g., in some embodiments, a system may include a computing device that does not require or include an operating system 104A. Computing system may COMPRISE Executable code 104B which may be any executable code, e.g., an application, a program, a process, task or script. Executable code 104B may be executed by processor 102, possibly under control of operating system 104A. Although, for the sake of clarity, a single item of executable code 104B is shown in FIG. 1. A system according to some embodiments of the invention may include a plurality of executable code segments similar to executable code 104B that may be loaded into memory unit 104 and cause processor 102, when executed, to carry out methods described herein.

In the following description of embodiments of the invention capabilities and features of such embodiments will be described with respect to biological structure of interest (BSOI), which may refer to any kind of biological structure that may be detected in a biological sample or specimen, such as cells of various types, tissues of various types, areas that do not contain certain types of cells, etc. The biological sample may typically be digitally scanned to produce a digital image of the sample, also known as slide. The slide may be subject to various computerized processes, such as pattern recognition, contour recognition and spotting, etc. The samples are typically stained in order to color one or more features of interest in the sample thereby to improve their detectability. As part of the process, samples may be presented to a respective expert, such as a pathologist, in order to assist the computerized process in identifying, annotating, categorizing and the like BSOIs that the computerized system miss, or find it hard to categorize.

According to embodiments of the invention a special process of annotating and categorizing is described in which an expert (herein after will be notated pathologist, for clarity of the description) and a computerized process are iteratively and dynamically cooperate, as described in detail herein below.

The description above was given with respect to processes of annotating and categorizing biological structures of interest from digital images of biological samples. It would be apparent to those skilled in the art that same or similar processes may enable the computerized system and processes described above, as cooperating with an expert from another field of expertise, to efficiently and rapidly categorize large number of different objects of interest that are included in a very large number of digitized slides. For example, a forester may cooperate with the system according to embodiments of the invention in order to categorize, spot, count and the like, several types of trees in a large area forest, based on the analysis of WSI extracted from satellite images. With a high enough resolution of the satellite images, this process may also be usable in, for example, detection of areas in the forest where trees suffer of pests.

In the description of various embodiments of the invention that follow, computing or processing operations that are described, may be performed, or carried out by a processor such as processor unit 102. Data items that are received may be stored in a memory such as memory unit 104 and/or storage unit 106. Data that is described presented to a user, such as an expert using the system described herein, may be presented using any suitable output means, such as output unit 130. For example, scanned slides of biological specimen, whether containing annotated objects or not, may be presented to a user on a screen or display. The screen or display may have resolution that meets the visual requirements associated with examined objects. Processes that involve computing and/or interactions between a computing unit and a user may be carried out by programs code stored in a memory unit or a storage unit and executable by the processing unit, possibly under the management of an operating system.

Figure 2A:
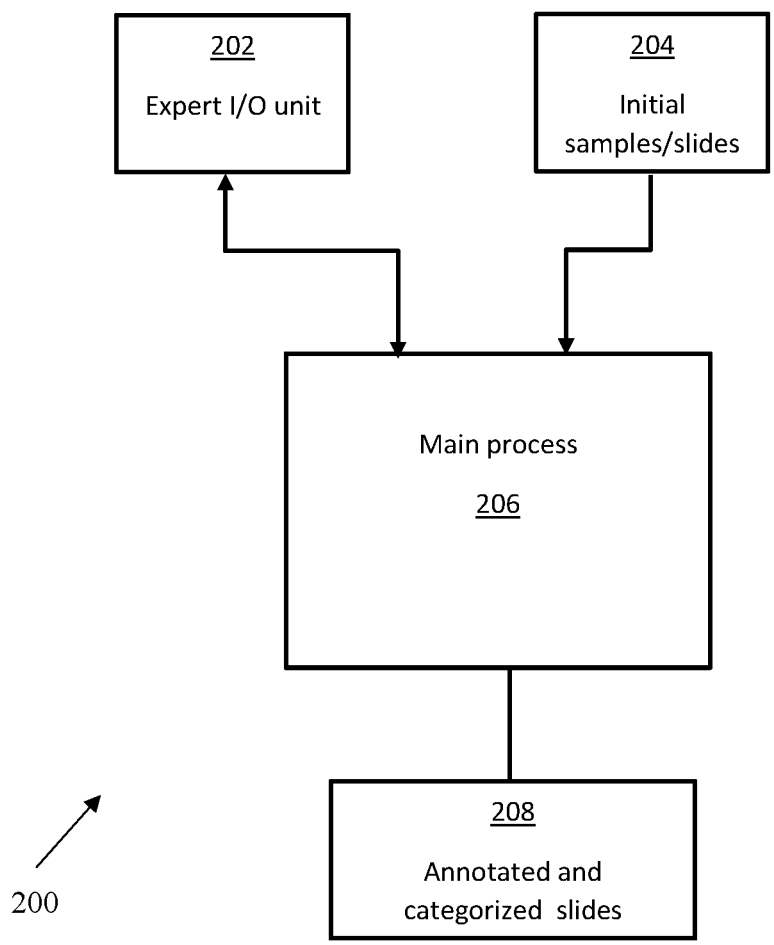
FIG. 2A is a schematic high-level block diagram depicting the cooperative nature of the flow of a BSOI detection, annotation and categorization according to embodiments of the present invention.

Reference is made to FIG. 2A which is a schematic high-level block diagram 200 depicting the cooperative nature of the flow of a BSOI detection, annotation and categorizing according to embodiments of the present invention. Samples or slides may initially be provided (block 204) to the main process (block 206) and concurrently an expert's input (block 202) may also be provided to the main process (block 206). The flow between expert's input and the main process is bidirectional, as is explained in detail below. The final result of the process may be annotated and categorized slides in which all of the BSOI's have been detected, annotated and categorized.

Figure 2B:
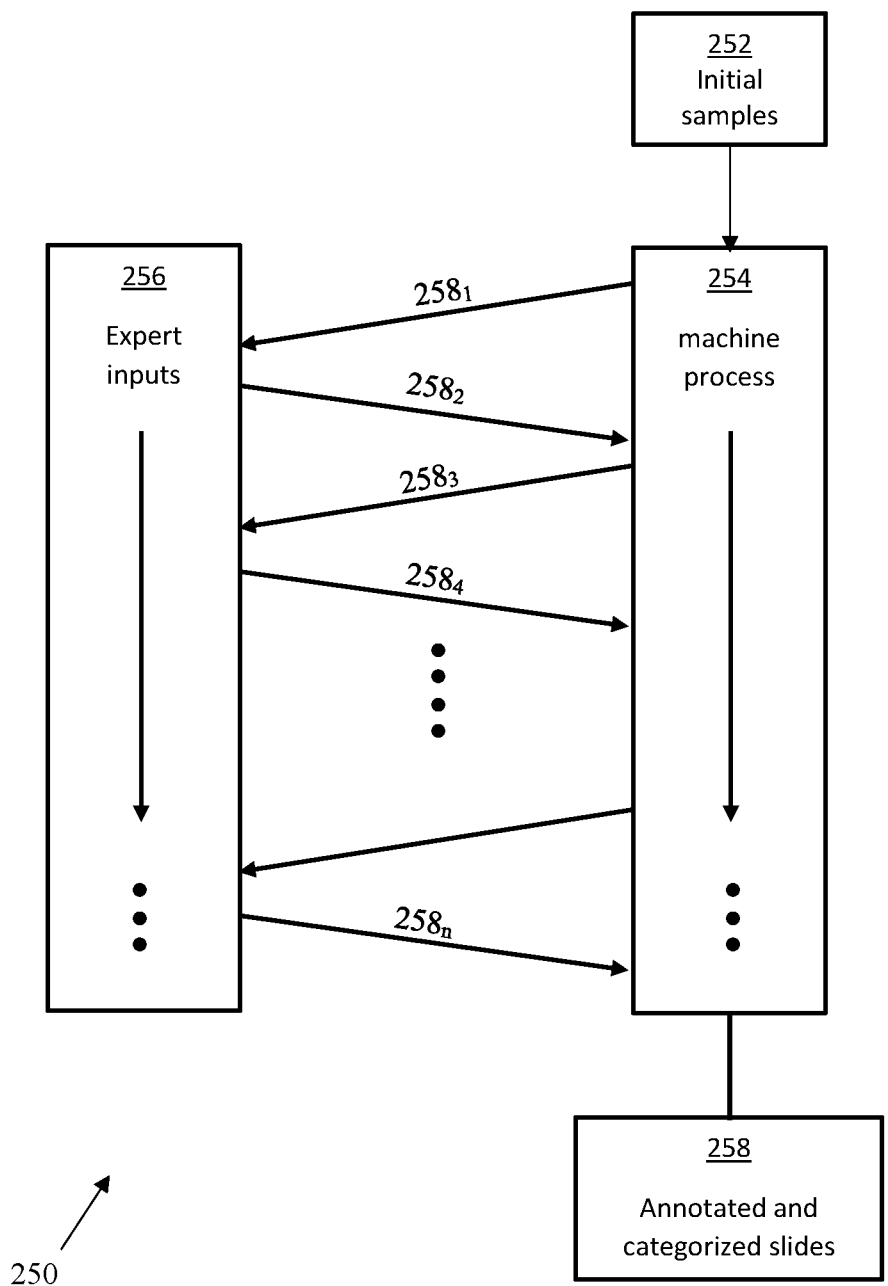
FIG. 2B schematically depicts another view of the flow of annotation and categorization process, according to embodiments of the present invention.

Reference is now made also to FIG. 2B, which schematically depicts another view of the flow of annotation and categorization process 250, according to embodiments of the present invention. Initial WSI of biological samples 252 may be provided to machine process 254. In other or additional embodiments initial WSI of biological samples 252 may be provided first to expert input process 256. Machine process 254 and expert process 256 may, each, perform its associated process which, as is explained in detail herein below, may also dynamically interact with each other as both processes progress, as depicted by interaction arrows $258_1$, $258_2$ ... $258_n$, where n may be a very big number, representing large number of iterations interacted between the expert and the computerized process.

Figure 2C:
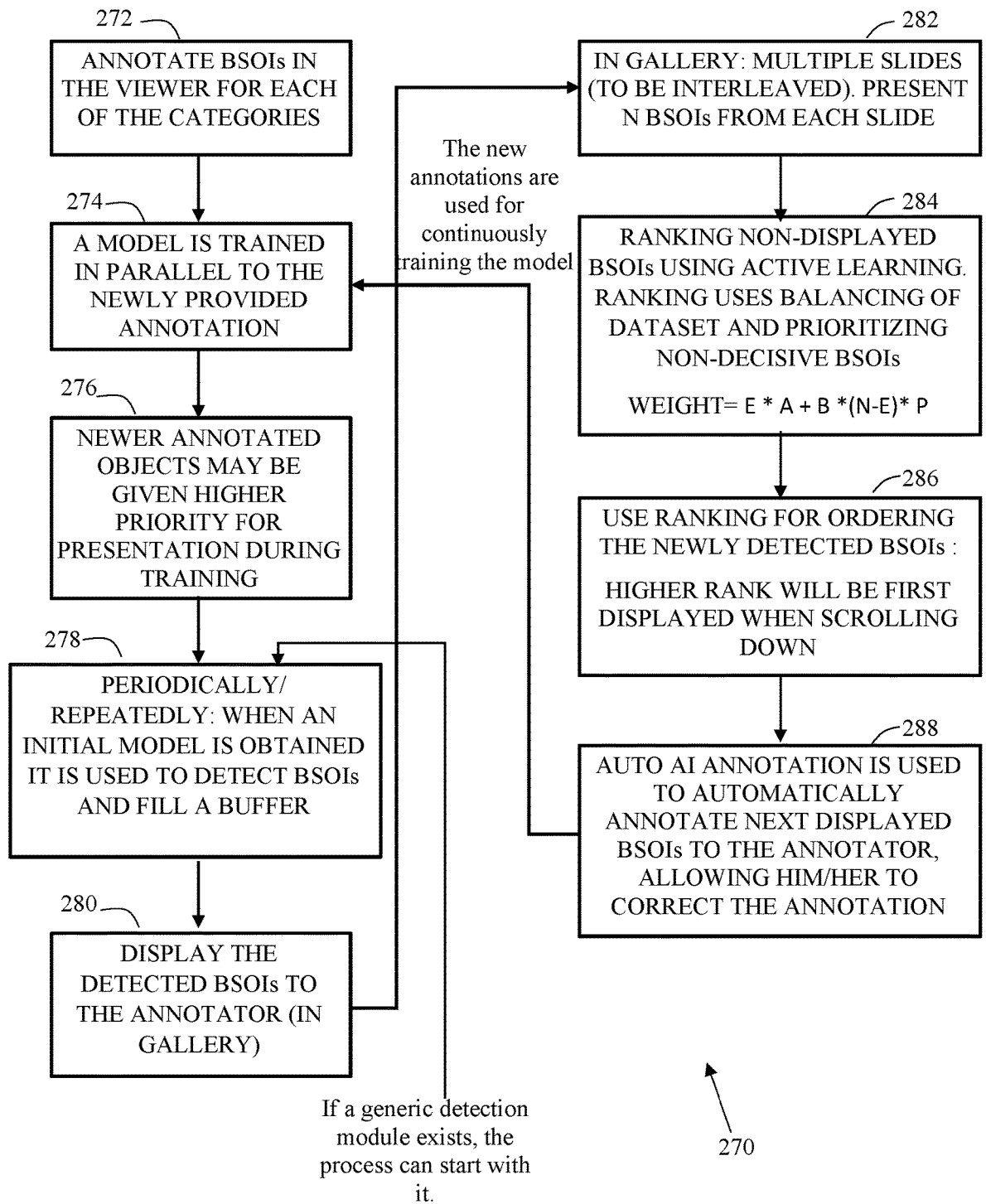
FIG. 2C is a schematic flow diagram, depicting the iterative interaction between operations and processes carried out by an expert and a computerized process according to embodiments of the present invention.

Reference is made now also to FIG. 2C, which is a schematic flow diagram 270, depicting the iterative interaction between operations and processes carried out by an expert (e.g. a pathologist) and the computerized process presented by blocks 272-280 on the left side of FIG. 2C, and a computerized process presented by blocks 282-288 on the right side of FIG. 2C, according to embodiments of the present invention. it will be apparent that at least some of the operations carried out by the expert, for example marking a BSOI in an image presented to the expert, may immediately be reported to the computerized process, for example as the marking finishes. The report may be in response to a mouse click, a touch of a touch screen, and the like. As will be explained in detail below, the computerized process may immediately respond to the reported expert's operation and as a result may present to the expert an updated image, or otherwise may present to the expert an updated dataset. In the following description operations carried out by the computerized process refer to 'gallery' as the means for accumulating and enabling presentation of slides, annotated (fully or partially) or not yet annotated, to the expert. Both flows of process, the expert's and the computerized, will be described as series of operations, however it will be realized that series of interactions may take place between the two flows, as described below.

Starting with the expert's flow of process, it may begin with annotating, by the expert, one or more types of BSOIs in slides that are presented to the expert, according to given categories (block 272). As a result of the freshly trained model, which was trained with the expert's annotated BSOIs, the active learning ranking algorithm may rank, or prioritize, the remaining un-annotated BSOIs and then displays slides containing them to the expert ordered by the ranking, so the annotation can be first done on the high ranked BSOIs (block 276). Once an initial model is formed, it may be used for the detection of BSOIs and for filling a buffer adapted to temporarily store slides which were just detected and are about to be ranked. The buffer may be established in a memory unit such as memory unit 104 of FIG. 1 or a storage unit such as storage unit 106 of FIG. 1. Since the model has been formed or set and is subject to be changed in response to newly annotated BSOIs, it may be reloaded periodically and repeatedly (block 278). Next, in block 280 the detected BSOIs may be displayed to the expert (also presented as annotator). The display is carried out by the gallery tool. The flow of process is directed now to the computerized flow, in block 282.

The computerized flow of process of diagram 270 may begin, for the sake of ordered description, by selecting slides kept in the gallery for processing (automatically annotate and categorize) multiple BSOIs in each slide (block 282). BSOI's that were not presented to the expert may be ranked using active learning and possibly also balancing algorithm of the dataset for prioritizing 'hard BSOIs' (BSOIs which the computerized flow was unable to decisively rank), for example using function (1) (block 286):

$$\text{WEIGHT} = E*A - B*(N-E)*P \text{ minority} \quad (1)$$

Wherein E=Entropy (class proportion), A=Acquisition function as defined in Active Learning, B=parameter, and Pminority=output of a neural network that detects cell categories that give the probability for the minority category. Function (1) will be further explained in detail below. The ranking obtained in block 286 may be used for properly ordering newly detected BSOIs, so that BSOIs with higher rank will be presented to the expert as he/she scroll further in the gallery, prior to BSOIs with lower priority. Auto AI-based annotation tool may be used to automatically annotate BSOIs that will be displayed next to the expert, while allowing the expert to intervene and correct/change automatically produced annotation (block 288).

As seen in FIG. 2C, the annotation in block 288 that was changed/corrected by the expert may now train the model in block 274, in response to the input just provided by the expert in block 288. When a generic detection module is available the flow of the expert's process may start, in some embodiments, in block 278, as explained in detail below.

Figure 3:
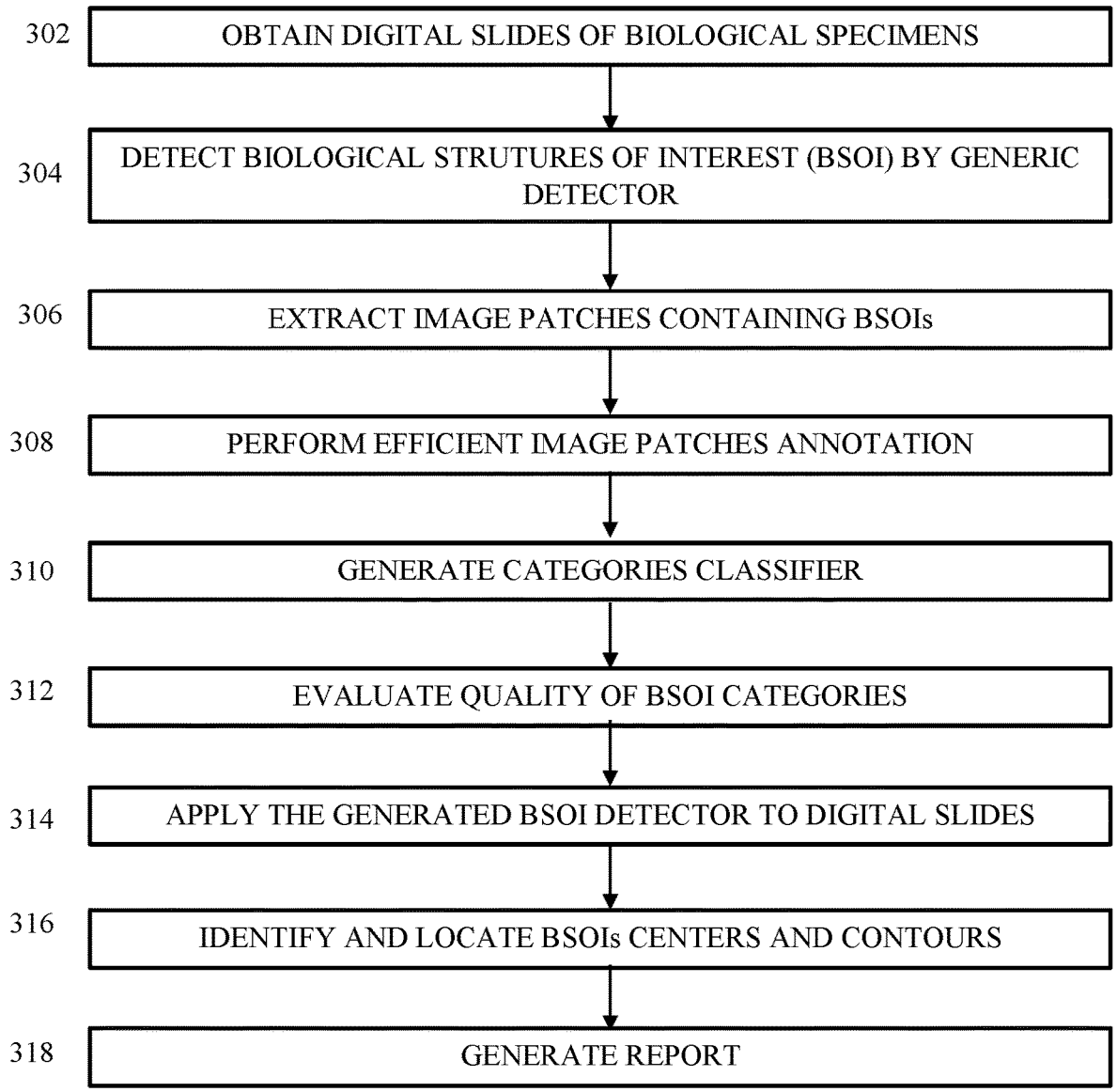
FIG. 3 illustrates a flowchart of a method for Cell Detection, according to embodiments of the present invention.

In the following description, of FIGS. 3-11, the examples of embodiments will refer to cells type of BSOIs. Reference is made now to FIG. 3, which illustrates a flowchart of a method for Cell Detection, according to embodiments of the present invention. As is explained below, a means for creation of a Deep Learning based tool for cell detection is formed according to requirements of the operating expert (the expert interacting with the computerized process). First, digital slides containing pathology samples may be received (block 302). The pathology slides are generated from tissue biopsies. The process of preparation of tissue biopsies may comprise sectioning, mounting on a glass slide and staining to enhance contrast in the microscopic image. For example, in some embodiments of the invention, a histological specimen slices may be stained by H&E, Giemsa or immune histochemical staining, to enhance certain features in the image. The slide may then be loaded on a digital scanner for digitization and the result is a digital file containing the image information.

The resultant image may then be submitted to a generic cell detection algorithm (block 304) that aims to detect all cells in the slide, of any category. A detailed description of the generic cell detector is given in the description of FIG. 4 below.

The result of block 304 is a list of the centers and contours of all the cells present in the slide. Image patches extraction module in block 306 is directed to extract crops that surround every selected cell. The size of the image patches (which may be expressed, e.g., by pixel units) can be set as a parameter and its default value may be set to 32×32 pixels, for example, or it may be set by a calculation on the typical size of the annotated cells, for example by taking the average of the cell size, or the average plus the standard deviation of the cell sizes. The image patches that may be created can then be submitted to interactive image annotation by the expert using a GUI (graphical user interface) application (block 308). Each time a single image crop is presented to the annotator and a man-machine interface (MMI) input means (keyboard press or mouse click, or touch screen tap, etc.) is used, the annotator may choose one category from a list of possible categories, each containing a specific type of BSOI (e.g. a cell) or background of the slide. A classification convolutional neural network (CNN) may be trained on all the of the available annotated image patches, to create a cell categories classifier (block 310). Online learning may be used to update the cell classification neural network as more annotations become available, as described in the description of FIG. 6. Efficient annotation may be enabled by active learning tool, as described in the description of FIG. 7, and active learning with data balancing strategy is described with respect to FIG. 8.

Figure 9:
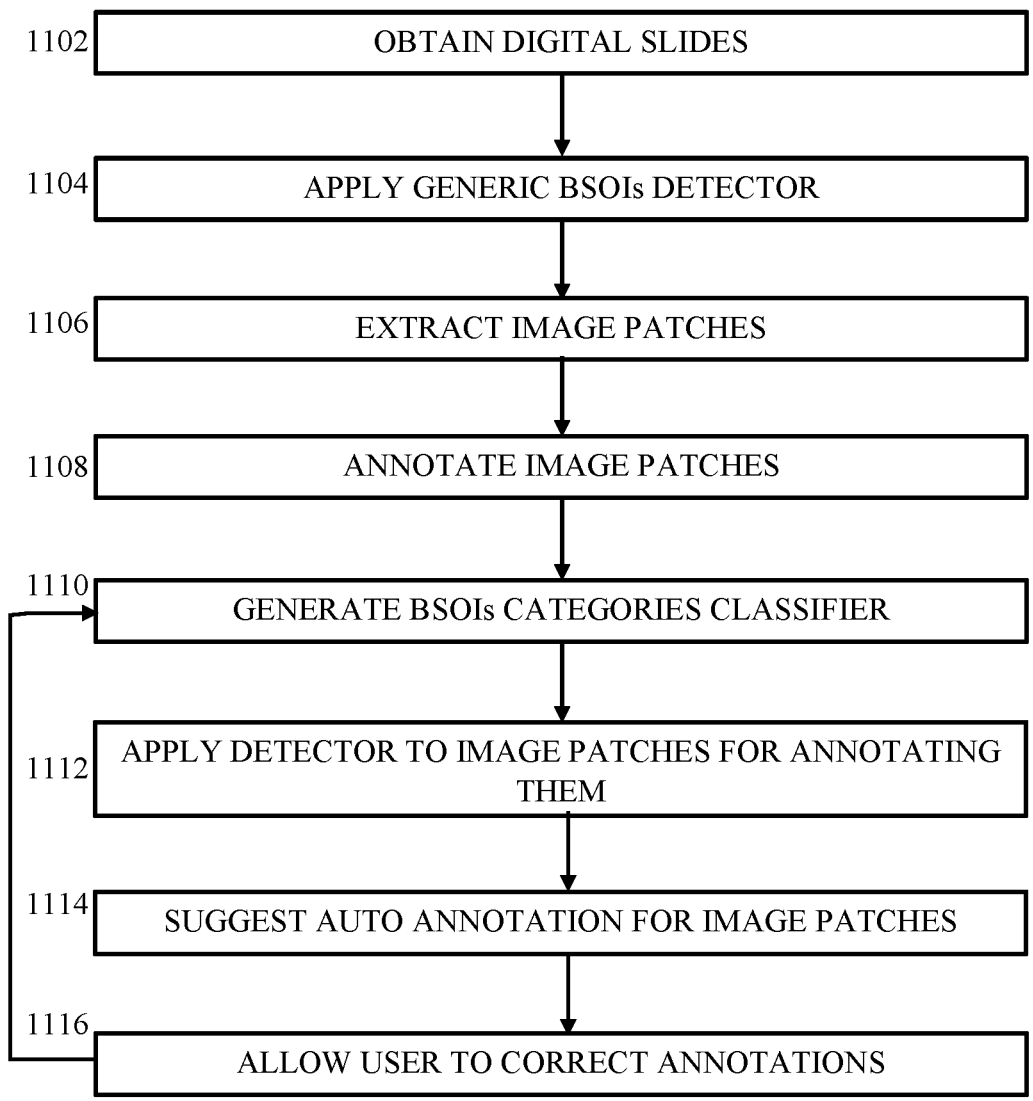
FIG. 9 illustrates a flowchart of a method for suggested auto annotation of cells, according to embodiments of the invention.

Moreover, efficient annotation may further be enhanced using an auto annotation scheme, when feasible, as described in detail with respect to FIG. 9. Once a Cell Categories Classifier is generated, the expert/annotator may test it on a new batch of slides to obtain visual and quantitative evaluation of the quality of the BSOI (e.g. cell) categories detector that is generated (block 312). The quantitative evaluation can be a receiver operating characteristic (ROC) curve, area under the curve (AUC) or any other standard metrics that may be used in deep learning. When the expert/annotator is satisfied with the quality of the generated cell detector, it can be applied to new digital pathology slides (block 314), where the centers and contours of the BSOI (e.g. cells) categories that are of interest only are located (block 316) and a report that may provide information on attributes of these cell category can be obtained (block 318). These attributes can be, but are not limited to: number, density, area, location and perimeter.

Figure 4:
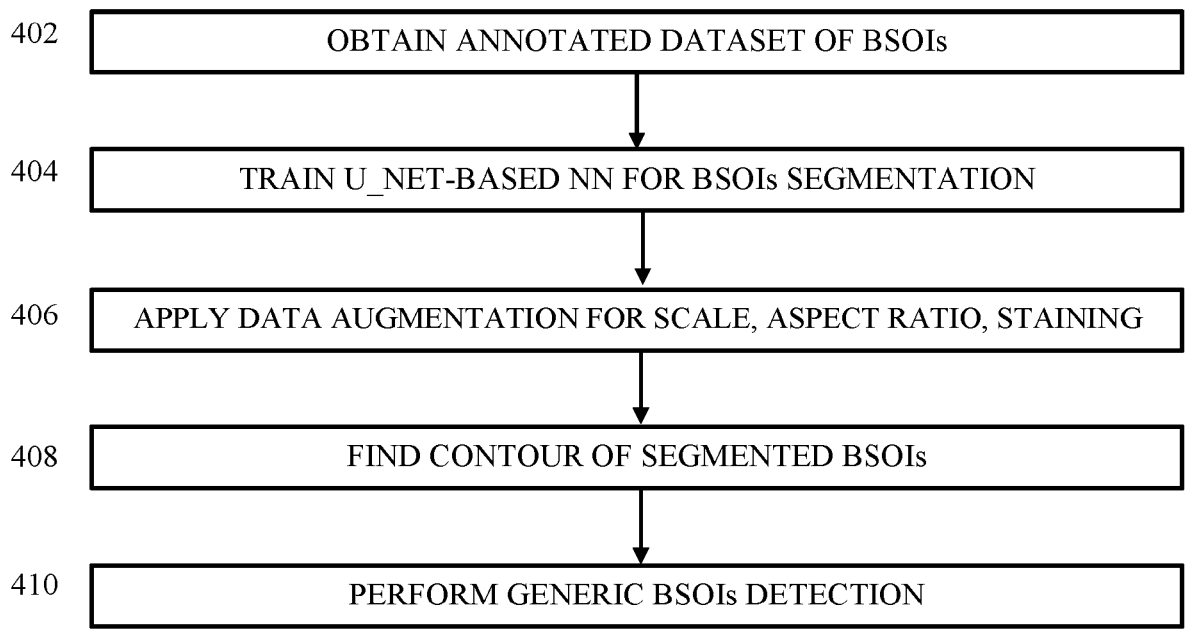
FIG. 4 illustrates a flowchart of a method for Generic Cell Detection, according to embodiments of the present invention.

Reference is made now to FIG. 4, which illustrates a flowchart of a method for Generic Cell Detection, according to embodiments of the present invention. (FIG. 3, block 304). An annotated dataset of cells of any kind may be obtained as input (block 402). A neural network based on a Unet architecture (as is known in the art) may be trained to obtain cell segmentation (block 404), and to provide contours of the segmented cells (block 406). Data augmentation methods may be used to add variability of scale, aspect ratio, staining and other variations, in order to generalize the cell segmentation neural network and make it robust to this possible variability (block 408). The result is a generic cell detector that can segment all cell types in a whole slide image (block 410).

Figure 5:
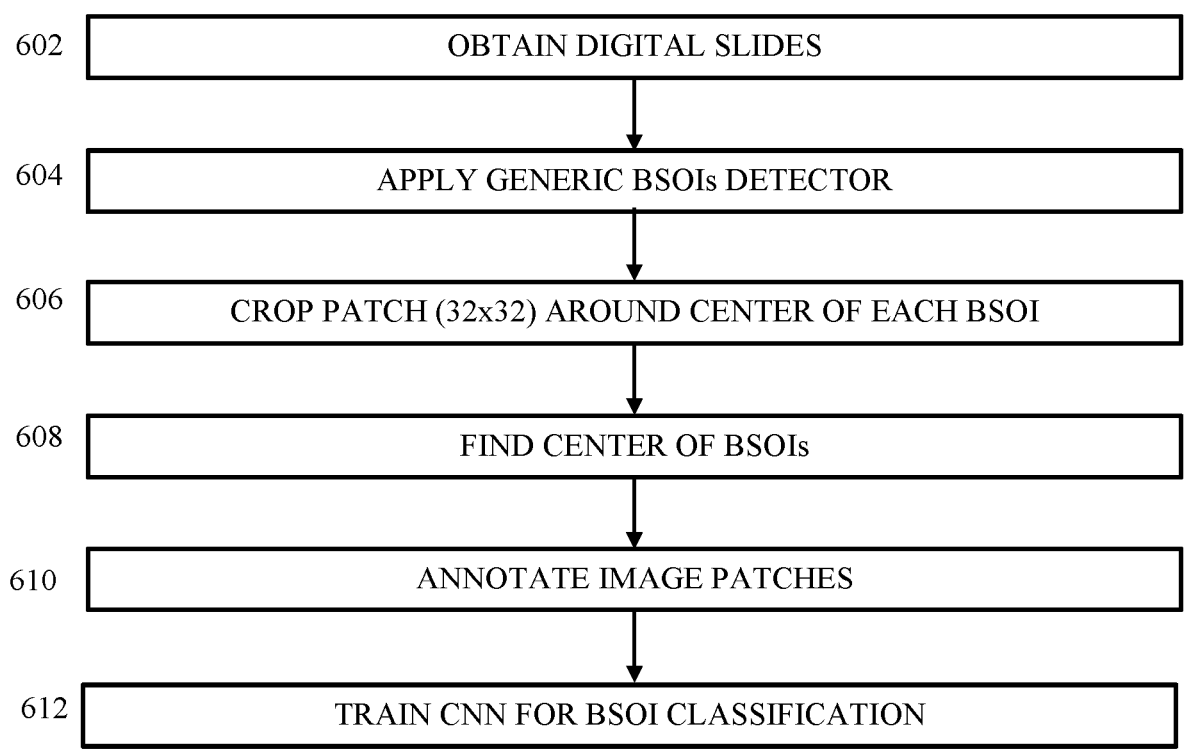
FIG. 5 illustrates a flowchart of a method for the training of a CNN for the classification of different cells categories, according to embodiments of the present invention.

Reference is made now to FIG. 5, which illustrates a flowchart of a method for the training of a CNN for the classification of different cells categories, according to embodiments of the present invention. The input is digital slides that contain cells of categories that are of interest to the expert (block 602). First, a generic cell detection algorithm (as described with respect to FIG. 4) may be applied to the slides (block 604). The result is a list of the centers and contours of all the cells in the slide (block 606). Next, image patches are generated around each cell center as crops of, e.g., 32×32 (block 608). The expert may now annotate the image patches, using a GUI, to associate to the cell categories of interest or background (block 610). This annotation may be used to train a CNN for cell categories classification (block 612).

Figure 6:
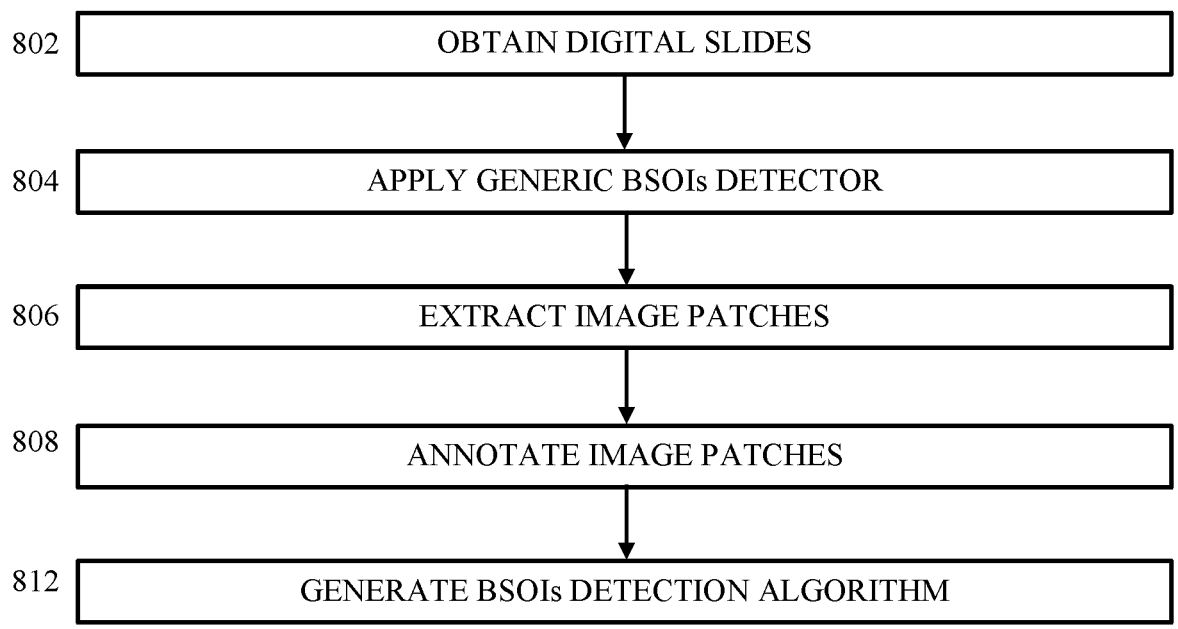
FIG. 6 illustrates a flowchart of a method for a Cell Detection Algorithm Generation using Active Learning, according to embodiments of the present invention.

Reference is made now to FIG. 6, which illustrates a flowchart of a method for a Cell Detection Algorithm Generation using Active Learning, according to embodiments of the present invention. Digital slides may be obtained (block 802), and a generic cell detector (e.g. as described with respect to FIG. 4) may be applied to a training set of slides to provide the centers and contours of all the cells in the obtained slides (block 804). Image patches around the centers of all the detected cells may be created (block 806) and may be submitted to annotation by the expert (block 808). Once a sufficient number of image patches is available, according to a predefined threshold, a detection algorithm for specific cell categories may be trained using this data (block 810). The deep learning neural network may then be continuously trained on the evolving dataset, as more annotations become available. During the training, the number of annotated cells in each cell category constantly changes and this can affect the loss of the neural network. The weights have to be constantly updated as the database constantly changes during online learning. Therefore, the loss is calculated as weighted cross entropy where the weights can be set using methods for class balancing, e.g. median frequency balancing. In addition, during the generation of the algorithm the architecture of the neural network, the number of layers, the number of parameters and the connection between layers may change. The expert can test the generated cell categories detector that was generated on new slides and may obtain visual and quantitative evaluation on the quality of the generated cell categories detector. The quantitative evaluation can be ROC, AUC or other standard metrics used in deep learning. When the expert is satisfied with the quality of the generated cell detector, the Cell Detection generation process is completed. The expert can resume the process with new data or modified annotations.

Figure 7:
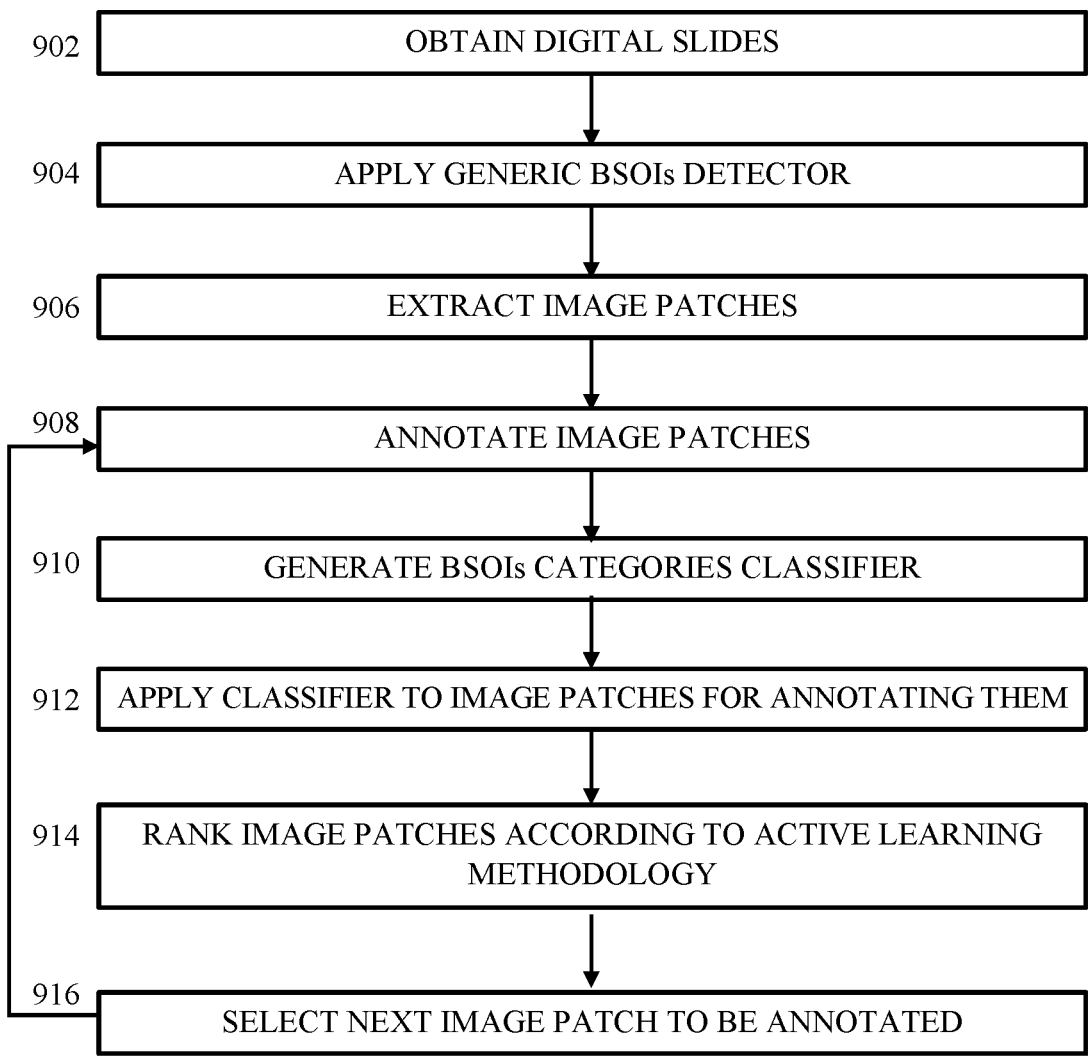
FIG. 7 illustrates a flowchart of a method for effective cell annotation using active learning, according to embodiments of the present invention.

Reference is made now to FIG. 7, which illustrates a flowchart of a method for effective cell annotation using active learning, according to embodiments of the present invention. Digital slides may be obtained (block 902) and the generic cell detector (as described with respect to FIG. 4) may be applied to a training set of slides to provide the centers and contours of all the cells in the obtained slides (block 904). Image patches around the centers of all the detected cells may be created (906) and may be submitted to annotation by the expert (908). Once a sufficient number of image patches is available, according to a predefined threshold, a detection algorithm for specific cell categories may be trained using this data (block 910). The current cell categories classifier may then be applied to image patches that were not annotated yet by the expert (block 912). These image patches may then be ranked according to active learning methodology (block 914). Each rank may have a life time of a pre-defined parameter that can be configured. When the life time elapses the rank is reset to a default value. The active learning algorithm chooses the best images to be annotated in order to make the annotation process most efficient. This ranking can be based on the acquisition function (should be minimized) or be carried out using an ensemble of models. If the ensemble of algorithms is in disagreement, this means that the algorithm is less confident for that image patch. The ensemble of algorithms can be generated using Bayesian deep learning, where drop out is applied at test time. The next image patches to be annotated by the expert may then be selected, according to this ranking (block 916), and the annotation procedure continues/returns to block 908. This process may continue until the expert is satisfied with the quality of the cell categories classifier generated.

Figure 8:
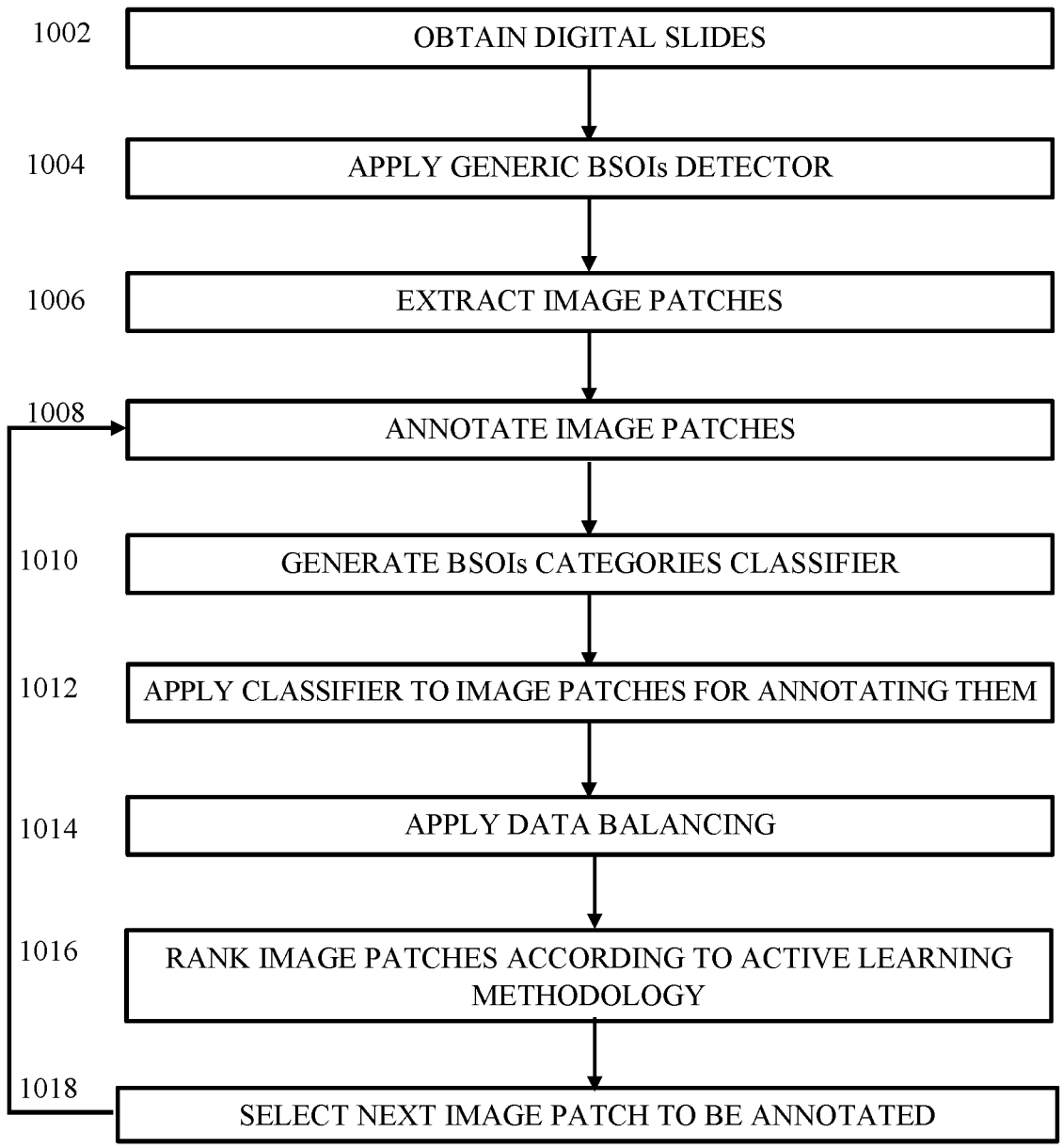
FIG. 8 illustrates a flowchart of a method of the invention for effective cell annotation using data balancing strategy for active learning, according to embodiments of the present invention.

Reference is made now to FIG. 8, which illustrates a flowchart of a method of the invention for effective cell annotation using data balancing strategy for active learning, according to embodiments of the present invention. Digital slides may be obtained (block 1002), and the generic cell detector (as described in FIG. 4) may be applied to a training set of slides to provide the centers and contours of all the cells in the slides (block 1004). Image patches around the centers of all the detected cells may be created (block 1006) and may be submitted to annotation by the expert (block 1008). Once a sufficient number of image patches is available, according to a predefined threshold, a detection algorithm for specific cell categories may be trained using this data (block 1010). The current cell categories classifier is then applied to image patches that were not annotated yet by the expert (block 1012).

Unbalanced data is a common situation where the number of instances of one category is significantly smaller than the number of instances of another category. In order to obtain a robust network there should be enough examples of each category. In order to overcome this problem data balancing methodology for effective active learning may be added (block 1014). The extent, or the level, of imbalance of a processed dataset may be expressed using any measure that is high when the dataset is balanced, and low otherwise. For the sake of the description herein, a high level of imbalance of a dataset means low presence of a given category in an examined dataset. Methods usable by a data balancing mechanism can be, for example, ranking the cells inversely proportional to their existence. Image patches that belong to the least frequent category may be duplicated. Data balancing mechanism using weighting component may also be added. The weight is inversely proportional to the proportion of least frequent category. Another approach may be to add data balancing using the following weighting:

$$\text{Weight} = E*A + B*(N-E)*P_{minority}$$

where:
    E=Entropy (class proportion)
    A=Acquisition function as defined in Active Learning.
    B=parameter
    N=number of categories
    $P_{minority}$=output of neural network that detects cell categories that give the probability for the minority category.

Acquisition function, as used here, examines a received image (e.g., slide) and returns a score that is: high when annotating the image by the model will improve the model because the model is unsure about the image, or the model didn't encounter images similar to it before, and low score when annotating the image isn't expected to improve the model.

Once there are enough examples of each category, the usual approach of active learning can be adopted. The image patches may then be ranked according to active learning methodology (block 1016) as was described with respect to FIG. 7. The next image patches to be annotated by the expert may then be selected according to this ranking (block 1018), and the annotation procedure continues (e.g., the process returns to block 1008). This process may proceed until the expert is satisfied with the quality of the cell categories classifier generated.

Reference is made now to FIG. 9, which illustrates a flowchart of a method for suggested auto annotation of cells, according to embodiments of the invention. Digital slides may be obtained (block 1102), and a generic cell detector (as described with respect to FIG. 4) may be applied to a training set of slides to provide the centers and contours of all the cells in the slides (block 1104). Image patches around the centers of all the cells detected may be created (block 1106) and may be submitted to annotation by the expert (block 1108). Once a sufficient number of image patches is available, according to a predefined threshold, a detection algorithm for specific cell categories may be trained using this data (block 1110). The current cell categories classifier may then be applied to image patches that were not annotated yet by the expert (block 1112). Once the cell categories detector is of sufficient quality, the activation of the auto annotation process can be triggered. This may be according to one of the following: 1) Time elapsed from beginning of training is higher than a threshold. 2) Classification results of the algorithm are close enough (according to a defined metric and threshold) to that of respective results of a human annotator; 3) Accuracy on a pre-defined validation set is good enough according to a pre-defined metric and threshold; 4) There is large enough number of annotations of cells of all categories of interest. Thus, the output of the current cell categories detector may be used to annotate the image patches not yet annotated (block 1114). The expert can correct the annotations as suggested by the system (block 1116) and these annotations may be submitted for further training of the cell categories classifier (return to block 1110). This process is ongoing until the user is satisfied with the quality of the cell categories classifier generated.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for categorizing biological structure of interest (BSOI) in digitized images of biological tissues comprising:
    detecting, by a generic detector, one or more BSOIs in at least one pre-obtained digitized image of biological tissue from a set of images;
    extracting image patches that contain, each, a BSOI;
    annotating the image patches according to the detected BSOIs;
    generating a BSOI categories classifier based on said annotation;
    applying the categories classifier to at least some of the digitized images;
    presenting an image that comprises at least one BSOI to a user, based on (i) a level of entropy of the BSOI, and (ii) a level of imbalance of a classified category of the image in the set of images;
    receiving from the user input indicative of a category to be associated with the at least one BSOI; and
    continuously annotating the image patches, to train the cell categories classifier according to the category of the BSOI provided by the user, as additional annotations become available,
    wherein presenting the image comprises:
    calculating a weighing component, configured to balance between a level of entropy of classified BSOIs and a level of imbalance of the classified category in the set of images;
    ranking BSOIs based on the weighing component; and
    displaying images containing BSOIs to the user ordered by the ranking.

2. The method of claim 1, wherein each of the plurality of images comprises, at least one BSOI with high level of entropy.

3. The method according to claim 1, wherein the weighing component is calculated by the function:

$$\text{Weight} = E*A + B*(N-E)*P\text{minority}$$

wherein
E=Entropy (class proportion)
A=Acquisition function as defined in Active Learning
B=parameter
N=number of categories
Pminority=output of a neural network that detects cell categories that give the probability for the minority category.

4. The method of claim 1, wherein presenting an image further comprises:
    automatically annotating BSOIs to be displayed to the user; and
    allowing the user to intervene, and change the automatically produced annotation.

5. A method for categorizing biological structure of interest (BSOI) in digitized images of biological tissues comprising:
    detecting, by a generic detector, one or more BSOIs in at least one pre-obtained digitized image of biological tissue from a set of images;
    extracting image patches that contain, each, a BSOI;
    annotating the image patches according to the detected BSOIs;
    generating a BSOI categories classifier based on said annotation;
    applying the categories classifier to at least some of the digitized images;
    presenting an image that comprises at least one BSOI to a user, based on (i) a level of entropy of the BSOI, and (ii) a level of imbalance of a classified category of the image in the set of images;
    receiving from the user input indicative of a category to be associated with the at least one BSOI; and
    continuously annotating the image patches, to train the cell categories classifier according to the category of the BSOI provided by the user, as additional annotations become available,
    wherein an order of presenting the images which comprise, each, at least one BSOI with high level of entropy, is responsive to the received user input indicative of a category of a B SOI, so that priority of presenting of images which await presenting to the user and comprise BSOI of the category that was indicated by the user, is made higher in response to the user's input.

6. A system for categorizing biological structure of interest (BSOI) in digitized images of biological tissues, said system comprising:
    a non-transitory storage device comprising program code stored thereon; and
    a processor configured to load the program code and execute the program code to perform:
    detecting, by a generic detector, one or more BSOIs in at least one pre-obtained digitized image of biological tissue from a set of images;
    extracting, image patches that contain, each, a BSOI;
    annotating the image patches according to the detected BSOIs;
    generating a BSOI categories classifier based on said annotation;
    applying the categories classifier to at least some of the digitized images;

presenting an image that comprises at least one BSOI to a user, based on (i) a level of entropy of the BSOI, and (ii) a level of imbalance of a classified category of the image in the set of images;

receiving from the user input indicative of a category to be associated with the at least one BSOI; and continuously annotating the image patches, to train the cell categories classifier according to the category of the BSOI provided by the user, as more annotations become available, wherein the processor is further configured to present the image by:

calculating a weighing component, configured to balance between a level of entropy of classified BSOIs and a level of imbalance of the classified category in the set of images;

ranking BSOIs based on the weighing component and displaying images containing BSOIs to the user, ordered by the ranking.

7. The system according to claim 6, wherein the weighing component is calculated by the function:

$$\text{Weight} = E*A - B*(N-E)*P\text{minority}$$

wherein

E=Entropy (class proportion)

A=Acquisition function as defined in Active Learning

B=parameter

N=number of categories

Pminority=output of a neural network that detects cell categories that give the probability for the minority category.

* * * * *